United States Patent [19]

Cross et al.

[11] Patent Number: 5,631,283

[45] Date of Patent: May 20, 1997

[54] USE OF SIALIC ACID OR ANTIBODIES TO SIALIDASE AS ANTI-INFECTIOUS AGENTS AND ANTI-INFLAMMATORY AGENTS

[75] Inventors: Alan S. Cross, Chevy Chase, Md.;
Daniel G. Wright, Nahant, Mass.;
Peter Gomatos, Ft. Lauderdale, Fla.;
Nicholas Stamatos, Washington, D.C.

[73] Assignee: The United States of America as represented by the Secretary of the Army, Washington, D.C.

[21] Appl. No.: 190,436

[22] Filed: Feb. 2, 1994

[51] Int. Cl.⁶ .................................................. A61K 31/35
[52] U.S. Cl. ............................................................ 514/459
[58] Field of Search ............................................. 514/459

[56] References Cited

U.S. PATENT DOCUMENTS 5,374,655 12/1994 Kashem et al. ........................... 514/540

FOREIGN PATENT DOCUMENTS 9222301 12/1992 WIPO .............................. A61K 31/70

OTHER PUBLICATIONS

STN compound [28283–68–3] 1994.

Ogura et al. 1987, Carbohydrate Resib. vol. 167 pp. 77–87.

Noble et al 1982 Eur. J. Biochem 126 pp. 543–548.

Ippolito et al 1994 120CA:261339X.

Primary Examiner—Russell Travers
Attorney, Agent, or Firm—John Francis Moran

[57] ABSTRACT

The administration of sialidase inhibitors or sialic acid is useful as means for treating inflammatory conditions and for intervening in infectious processes in instances where pathogenicity of the disease-causing organism is increased by microbial surface interaction with host cells.

12 Claims, No Drawings

USE OF SIALIC ACID OR ANTIBODIES TO SIALIDASE AS ANTI-INFECTIOUS AGENTS AND ANTI-INFLAMMATORY AGENTS

FIELD OF THE INVENTION

This invention relates to the alteration of eukaryotic cell surfaces by administration of sialidase inhibitors or sialic acid.

BACKGROUND OF THE INVENTION

Part of the inflammatory process is accomplished by the circulating white blood cells, especially neutrophils, by (1) slowing down at a site within the blood vessel where an inflammatory response is developing, (2) adhering to the endothelial cells adjacent to the site of inflammation, (3) exiting the intravascular space through the lining of the blood vessels and (4) migrating to the inflammatory site within the tissues. In order to achieve this complex series of steps, the neutrophil must bind to the endothelial cells lining the vessels and then "unbind" so that it can continue on into the tissue. It is known that sialic acid residues on glycoconjugates of the cells are important in this initial binding.

The term "sialic acid" denotes members of a family comprising natural derivatives of neuraminic acid, an acid amino pyranose with 9 carbon atoms. In nature, the amino group is substituted either with an acetyl or glycolyl residue. The hydroxy groups may be methylated or esterified with groups such as acetyl, lactyl, sulfate, or phosphate groups. Multiple substitutions are common.

Sialic acids are a phylogenetically conserved family. These amino sugars are conjugated to protein and lipid moieties on the surface of mammalian cells and are potent modulators of biologic behavior. There is substantial evidence that sialic acids are structural determinants of important cell-to-cell interactions and cellular functions such as adhesiveness. There is considerable evidence that sialic acid residues protect molecules in circulation from recognition, clearance or degradation and that they regulate complement deposition on cell surfaces. Sialic acid residues also modulate attachment of microbial toxins as well as parasites to these cell surfaces.

The cleavage of the sialic acid by sialidases or neuraminidases from the glycoconjugates results in decreased rigidity of the cell surface, thereby facilitating cell motility, and effects cell-to-cell interactions such as adhesiveness and metastatic potential. Sialidases or neuraminidases are produced by many microbes and by mammalian cells. Whereas the presence of endogenous sialidase of mammalian cells has been well described, its role has best been studied primarily in a clinically heterogenous group of inherited disorders designated as sialidoses, wherein an abnormal amount of sialic acid accumulates in tissues of patients resulting in neurologic defects and premature death.

Endogenous sialidase in phagocytes has previously been described. It has been found that, upon activation such as may occur during infection or inflammation, this enzyme is translocated to the cell surface from sites within the cell (Cross and Wright, *Journal of Clinical Investigation, Inc.*, 88 (December, 1991) pp 2067–2076). The result of this mobilization is the removal of significant quantities of cell-associated sialic acid from glycoconjugates on cell surfaces. Desialylation of resting cells by microbial neuraminidase or of activated cells by mobilization of endogenous sialidases remove negative electric charges from cell surfaces and alters the biologic behavior of these cells to that typically observed during inflammation. Activation of cells in the presence of known sialidase inhibitors such as exogenous sialic acid prevents the desialylation and lowers cell adherence.

Infection of mammalian cells by HIV is known to be facilitated by activation of its cellular target. The critical events in the multistep process of cellular activation that facilitates infection with HIV have not been identified. It has been shown that increased expression of endogenous sialidase follows activation of T lymphocytes by lectins and it has been suggested that this increase may play a role in the differentiation and maturation of these cells. Sialidase-treated peripheral blood mononuclear cells (PBMCs) support growth of HIV-1 in the absence of lectin activation. Treatment of PBMCs with sialidase or lectin (phytohemagglutinin) results in hyposialylation of the PBMC.

Specific inhibitors of sialidase activity have been used in vivo in mice to decrease mutual adhesion of blood platelets and to inhibit accumulation of leucocytes in microvascular beds that had been laser-irradiated. (Gorog, et al, *Br. J. exp. Path.* 61 (1980), 490).

Various sialidase inhibitors have previously been tested. Kumar, et al. (*Carbohydrate Research*, 94 (1981) 123–130) disclosed a method of synthesizing various neuraminic acids. Noble, et al. *J. Biochem*, 126 (1982) (543–548) discloses methods of synthesis of 2-deoxy-2,3-dehydro-N-acetylneuraminic acid and 2-deoxy-2,3-dehydroneuraminic acid and discusses the oral administration and secretion of the sialic acids. No method of using these inhibitors for anti-infective or anti-inflammatory use are taught therein. Nagai, et al. (*Biocehmical and Biophysical Research Communications*, Vol 163, No. 1 (1989) and Miyaichi, et al. (Shoyakugaku Zasshi, 42 (3)(1988) 216–219) disclose use of a natural product from the leaf of *Scutellaria baicalensis* as an inhibitor of mouse liver sialidase, but its application to the treatment of inflammation is not discussed.

SUMMARY OF THE INVENTION

This invention provides a means of treating inflammatory conditions and of intervening in infectious processes in instances where pathogenicity of the disease-inducing organism is increased by microbial surface interaction with host cells. Sialic acids may be delivered at dosage of 0.1 to 10 mg/kg intravenously 4–6 time a day. For humans, dosage forms would contain 5 to 1000 mg of sialic acid or sialic acid analogue. For example, presence of 2,3-dehydro-2-desoxy-N-acetyl neuraminic acid (NANA) prevented desialylation of peripheral blood lymphocytes and ability of the cells to support infection by HIV. A second aspect of the invention relates to inhibition of sialidases by administration of antibodies which inhibit the action of sialidases.

DETAILED DESCRIPTION OF THE INVENTION

Sialic acids such as NANA have the ability to prevent hyposialylation of cells by competitive inhibition of the endogenous sialidase. The desialylation of cells is shown to increase adhesive properties of the cells and to render cells more susceptible to invasion by infectious organisms, particularly HIV. Cellular hyposialylation also accompanies inflammation. The sialidase inhibitors used as disclosed herein are effective in treating and/or in avoiding inflammation. It is possible that for the cell to "unbind" to leave the vascular space it must deadhere or "unbind" in a manner that might involve the cleavage of sialic acid residues. The enzyme that would accomplish this cleavage is sialidase. It is reasonable to believe that inhibition of this enzymatic step results in a decreased ability of neutrophils to leave the intravascular space and migrate to inflammatory sites within tissue. Thus, any agent that inhibits sialidase can act as an anti-inflammatory agent.

Sialic acid and its analogues are of the formula:

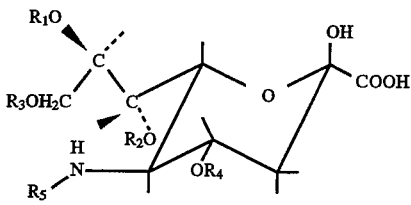

wherein $R_{1,2,3, \text{ and } 4}$ may be H, alkyl, $SO_3H$, $PO_3H_2$ or CO-alkyl, wherein alkyl has 1–4 carbons and may be substituted with OH and $R_5$ is CO-alkyl of 1–carbons which may be substituted with OH, with acetyl, and glycolyl being preferred at $R_5$.

MATERIALS AND METHODS

Isolation snd Culture of PBMCs

Peripheral blood mononuclear cells were isolated from whole blood of HIV-1- and hepatitis B-seronegative donors by Ficoll-Paque (Pharmacia, Piscataway, N.J.) density gradient centrifugation and were grown in RPMI 1640 medium (GIBCO, Grand Island, N.Y.) containing 10% purified, delectinized human IL-2 (Advanced Biotechnologies, Inc., Columbia, Md.) and 15% heat-inactivated fetal bovine serum (GIBCO). Cells were maintained at 37° C. on $CO_2$-humidified incubator for 24 to 72 hours prior to treatment with phytohemagglutin (PHA) or neuraminidase, respectively.

Pretreatment of PBMCs With PMA Or Neuraminidase

Cells at $10^7$ cells/ml were treated with PHA at 5 µg/ml for 30 minutes, were diluted 5-fold by addition of medium and were maintained in media containing PHA at 1 µg/ml. After 48 hours, cells were removed from the PHA-containing medium by centrifugation prior to infection with HIV-1. Alternatively, after 72 hours in culture, untreated cells were collected and resuspended at $10^7$ cells/ml for treatment at 37° C. for 30 minutes with 1 U/ml microbial neuraminidase, unless other treatment conditions were indicated. Cells were removed from the enzyme by centrifugation and were washed once prior to infection. Macrophage-depleted cultures were prepared for treatment with PHA or NANAse by collecting PBMCs which had not adhered to culture flasks after 24 or 72 hours, respectively. Cells exposed to PHA at 24 hours for stimulation during the subsequent 48 hours to provide 72 hours from seeding of cells to infection. Cells treated with sialidase were treated with enzyme 72 hours after seeding (immediately before infection). After 72 hours, PHA-or sialidase-(NANAse) treated cells were seeded in 96 well microtiter plates at $2.5 \times 10^5$ cells/well and were infected with HIV-1. Alternatively, infected cells were maintained in 75 cc flasks at $1 \times 10^5$ cells/mi.

HIV Infection of PBMCs

HTLV-IIIB/H9 strain HIV adapted to T cell lines were used to infect the PBMCs in the wells of microtiter plates at 50, 5, 1 or 0.5 $TCID_{50}$ of HIV-1 in final volume of 0.25 ml in media containing POLYBRENE$^R$ (Sigma) at 1 µg/ml. (When infected cells were maintained in flasks, $0.8 \times 10^7$ cells were infected with $1.6 \times 10^3$, $1.6 \times 10^2$, and $1.6 \times 10$ $TCID_{50}$ in a volume of 2 ml for 2 hours at 37° C. to remove unadsorbed virus, cells were centrifuged, washed once, and seeded in 75 cc flasks at $1 \times 10^6$ cells/ml.) In both the microtiter plates and in the flasks, cells were incubated at 37° C. for 21 days. One half volume of media was removed one day post infection and every 2 days thereafter to be replaced with an equal volume of fresh medium. Levels of p24 Ag in culture fluids were determined by ELISA (Coulter Immunology, Hialeah, Fla.).

Determination of Total Cell-Associated Sialic Acid

Cells treated with PHA, NANAse or untreated cells were washed three times in cold RPMI before exposure of pelletted cells to 0.1 M $H_2SO_4$ at 80° C. for one hour to release cell-associated sialic acid. Free sialic acid was measured by the Warren Assay.

Determination of Cellular Sialidase Activity

PBMCs in RPMI 1640 medium containing 10% fetal bovine serum and 4 U/ml of recombinant human IL-2 (Boehringer Mannheim, Indianapolis, Ind.) were incubated at 37° C. for 48 hours alone or with PHA (7.5 µg/ml). After 48 hours, cells were reisolated in a density gradient of Lymphocyte Separation Medium and were washed twice. After resuspension of cells in RPMI 1640 at $80 \times 10^6$ cells/ml, sialidase activity was assayed by incubating intact cells with neurminyl-lactose (Sigma) 1 mg/ml at 37° C. for 2 hours. Sialidase activity was determined by correlating the amount of sialic acid released from intact cells to a standard curve generated by determination of sialic acid released from neuraminyl lactose by 10 mU/ml NANAse.

Results

Treatment of cells with sialidases rendered the peripheral blood mononuclear cells susceptible to infection with HIV, while administration of sialic acids counteracted the effects of sialidase. (See Tables I and II.)

TABLE I

| | Susceptibiltiy of pretreated PBMC's in neuraminidase and PHA: | | | |
|---|---|---|---|---|
| Experiment: | HIV-1 inoculum ($TCID_{50}/2.5 \times 10^5$ cells) | p24 Ag (ŋg/ml) released from cells pretreated with: | | |
| | | None | PHA | NANAse |
| #1 | 50 | 32 | 73 | 41 |
| | 5 | 7 | 72 | 20 |
| | 1 | 0 | 69 | 26 |
| #2 | 59 | 12 | ND | 15 |
| | 5 | 0 | ND | 16 |
| | 0.5 | 0 | ND | 12 |
| #3 | 0.5 | 0 | 5 | 50 |

It has also been found that the effect of sialidases can be counteracted by administration of competitive inhibitors of sialidases, specifically by administration of analogues of sialic acid. Neuraminic acid (NeuAc) and 2,3-dehydro-2-desoxy-N-acetyl-neuraminic acid (NeuAc2en) were tested as competitive inhibitors of neuraminidases. Growth of HIV was not detected in cells which had been pretreated with NANAse in the presence of 250 µM NeuAc or NeuAc2en. Hence, presence of the competitive inhibitors of the NAN- Ase protected cells from vulnerability to the HIV-1. (See Table II.)

TABLE II

Protective effect of sialic acid analogues on growth of HIV:

| Conditions of NANAse pretreatment of PBCM's | p24 Ag (ηg/ml) released | |
|---|---|---|
| | day 12 | day 22 |
| 1 U/ml, 240 min | 54 | 56 |
| 1 U/ml, 30 min | 59 | 56 |
| 0.1 U/ml, 30 min | 0 | 0 |
| 1 U/ml + NeuAc (250 μM), 30 min | 0 | 0 |
| 1 U/ml + NeuAc2en (250 μM), 30 min | 0 | 0 |
| Heat-inactivated NANAse, 30 min | 0 | 0 |

Sialic acid analogues are effective at dosages of about 0.1 to 10 mg/Kg for 4 to 6 hours. Administration intravenously of the sialic acid analogue can be used to effectively protect cells from infection with HIV. By methods of the invention, the patient with HIV may be placed on a regimen to protect the cells through one replacement cycle for the PBMC's.

Synthesis of viral DNA is initiated following infection of both activated and quiescent primary lymphocytes, but HIV genomic RNA is not transcribed completely for full-length double-stranded DNA in quiescent PBMC. HIV can remain latent in quiescent cells for an extended period of time, but if mitogenic stimulation occurs within 4–8 days of infection, synthesis of viral DNA is completed and growth of virus occurs. Hence, administration of sialic acid analogues can be used to protect cells during early stages of infection (the period immediately after exposure to HIV) from completion of the viral growth cycle.

Modulation of Inflammatory Response

The injection of thioglycollate into the peritoneum of animals is a well-established experimental technique for eliciting an inflammatory response. Therefore, mice were pre-treated intravenously with either a competitive inhibitor of sialidase (sialic acid was used) or with a polyclonal rabbit anti-sialidase antisera in an attempt to have inhibitors of sialidase circulating in the blood at the time of initiation of the inflammatory process with thioglycollate. It was reasoned that if these agents were effective in inhibiting sialidase and if sialidase were important in the inflammatory response, a decreased amount of cells migrating into the peritoneal site of inflammation would be seen.

Preventive Effects in Mice

Three groups of mice were studied for response to injections of thioglycollate in amounts sufficient to cause an inflammatory response. All groups were pretreated:

Group 1: Mice were pretreated intravenously with normal rabbit serum.
Group 2: Mice were pretreated intravenously with rabbit antisera containing increased levels of antibodies to sialidase.
Group 3: Mice were pretreated intravenously with sialic acid.

Results

Mice in groups 2 and 3 showed less inflammatory response that the mice treated with normal rabbit serum. Hence, it was seen that both antibodies to sialidase and sialic acid showed anti-inflammatory effects. Such anti-inflammatory effects are needed for patients suffering from inflammatory responses of tissues such as autoimmune response, arthritis (including rheumatoid arthritis) and pneumonitis (including idiopathic conditions such as sarcoidosis).

Sialic acid and sialic acid analogues may be given intravenously or into the site of inflammation. For example, the active agents may be administered into, for example joints or the peritoneal cavity.

We claim:

1. A method of treating inflammation by administration of an anti-inflammatory composition in dosage form comprising an anti-inflammatory effective amount of sialic acid or a sialic acid analogue of the formula:

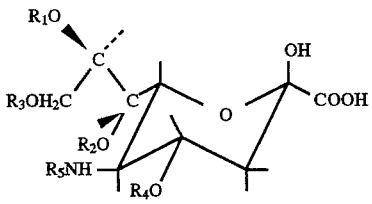

wherein $R_{1,2,3 \text{ and } 4}$ is H, alkyl, $SO_3H$, $PO_3H_2$ or CO-alkyl, wherein alkyl has 1–4 carbons and may be substituted with OH, and $R_5$ is CO-alkyl of 1–4 carbons which may be substituted with OH in a pharmaceutically acceptable carrier.

2. A method of claim 1 wherein $R_5$ is acetyl or glycolyl.

3. A method of treating inflammation by administration of an anti-inflammatory composition in dosage form comprising an anti-inflammatory effective amount 2,3-dehydro-2-desoxy-N-acetylneuraminic acid in a pharmaceutically acceptable carrier.

4. A method of claim 1 wherein therein the anti-inflammatory composition is administered locally into a site of inflammation.

5. A method of claim 4 wherein the anti-inflammatory composition is administered into a joint.

6. A method of claim 1 wherein the anti-inflammatory composition is administered intravenously.

7. A method of claim 3 wherein the composition is administered intravenously.

8. A method of claim 3 wherein the composition is administered into locally to a site of inflammation.

9. A method of claim 8 wherein the composition is administered into a joint.

10. A method of claim 2 wherein the composition is administered intravenously.

11. A method of claim 2 wherein the composition is administered into locally to a site of inflammation.

12. A method of claim 11 wherein the composition is administered into a joint.

* * * * *